United States Patent [19]
Fain et al.

[11] Patent Number: 5,290,299
[45] Date of Patent: Mar. 1, 1994

[54] DOUBLE JAW APPARATUS FOR ATTACHING IMPLANTED MATERIALS TO BODY TISSUE

[75] Inventors: Eric S. Fain, Menlo Park; Mary E. Bush, Fremont, both of Calif.

[73] Assignee: Ventritex, Inc., Sunnyvale, Calif.

[21] Appl. No.: 16,484

[22] Filed: Feb. 9, 1993

Related U.S. Application Data

[63] Continuation of Ser. No. 804,934, Dec. 11, 1991, abandoned.

[51] Int. Cl.⁵ .............................................. A61B 17/00
[52] U.S. Cl. .................................... 606/142; 606/139; 606/1; 606/207; 227/902
[58] Field of Search ............ 606/139, 142, 143, 1, 606/205–207; 128/46; 227/902

[56] References Cited

U.S. PATENT DOCUMENTS

| | | | |
|---|---|---|---|
| 1,303,135 | 5/1919 | Wappler | 606/206 |
| 3,999,555 | 12/1976 | Person | |
| 4,712,545 | 12/1987 | Honkanen | 606/208 |
| 4,722,339 | 2/1988 | Dreier et al. | 606/208 |
| 4,865,037 | 9/1989 | Chin et al. | |
| 5,037,433 | 8/1991 | Wilk et al. | 606/139 |
| 5,099,827 | 3/1992 | Melzer et al. | 606/142 |

Primary Examiner—Stephen C. Pellegrino
Assistant Examiner—Jeffrey A. Schmidt
Attorney, Agent, or Firm—Steven M. Mitchell; Mark J. Meltzer

[57] ABSTRACT

A system is provided for fastening an implantable medical device, for example a defibrillator lead, to the heart. A lead electrode is placed in a desired position against the pericardium, pericardial tissue is grasped with a fastening tool, and the pericardial tissue is drawn away from epicardium and toward the fastening tool. A fastening member is applied to the pericardial tissue and to the lead electrode to secure the lead in the desired position. The application tool comprises a first pair of jaws for grasping membranous tissue and drawing the tissue away from other tissues and toward the tool. A second pair of jaws is provided for holding fastener members and delivering the fastener members to the membranous tissue.

2 Claims, 8 Drawing Sheets

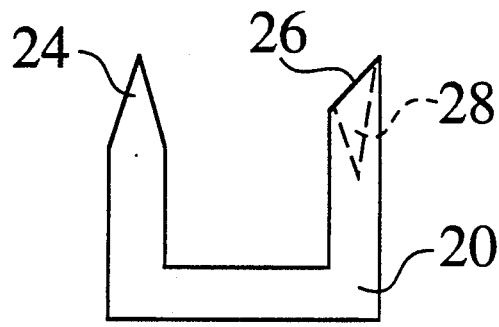
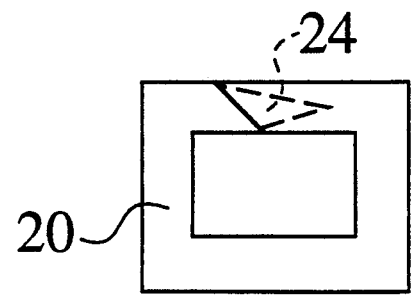
Fig. 1  Fig. 2
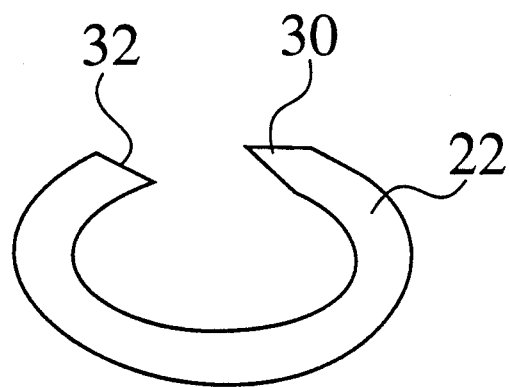
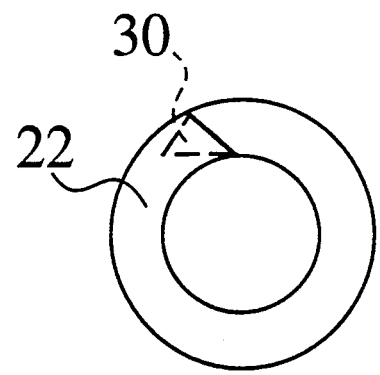
Fig. 3  Fig. 4

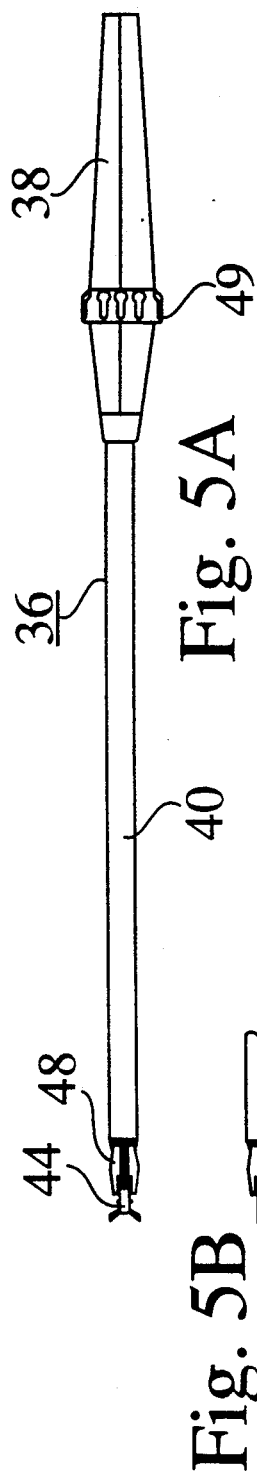
Fig. 5A
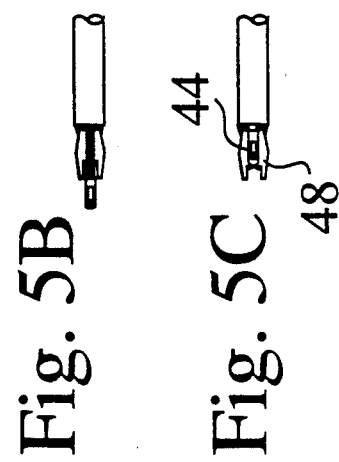
Fig. 5B
Fig. 5C
Fig. 5D
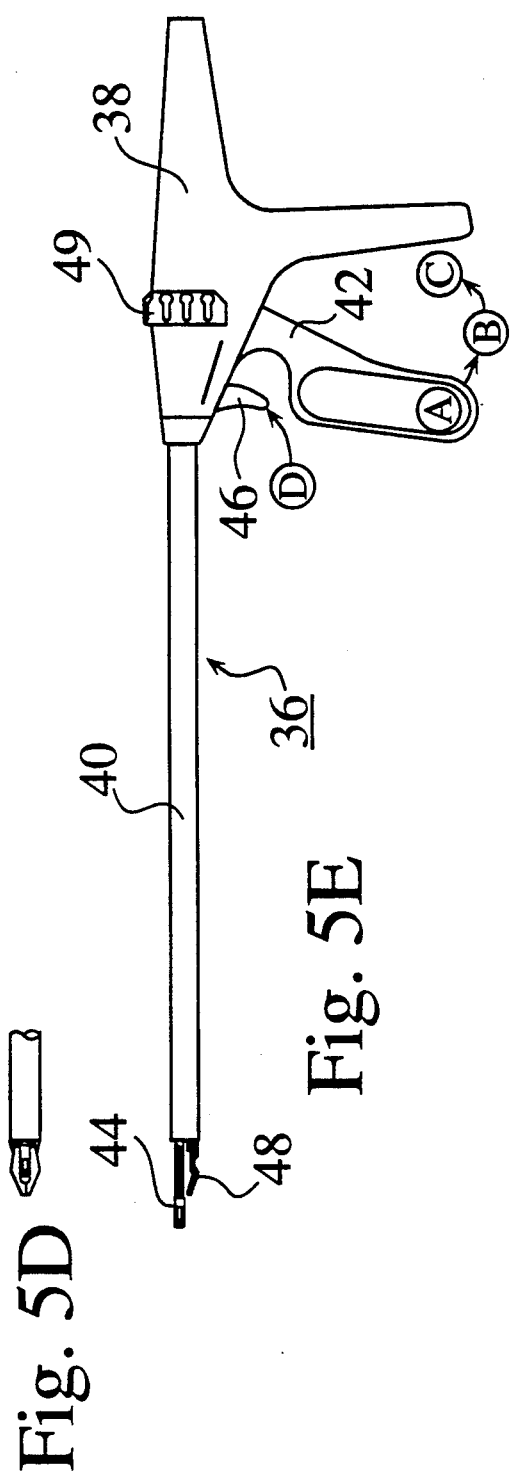
Fig. 5E

DOUBLE JAW APPARATUS FOR ATTACHING IMPLANTED MATERIALS TO BODY TISSUE

This is a continuation of application Ser. No. 07/804,934, filed on Dec. 11, 1991, now abandoned.

FIELD OF THE INVENTION

This invention relates to a method and apparatus for attaching implanted materials or devices to tissue inside the body. One specific application of the invention is to provide a means and apparatus for attaching and fixating defibrillation leads adjacent to the heart after their introduction into the body via a large incision or small aperture. A more general application is for a safer method for affixing clips or fasteners to body tissue.

BACKGROUND OF THE INVENTION

It is well-known in the field of cardiology that ventricular tachyarrhythmias can be effectively treated by the application of electrical shocks to the heart. Such defibrillation may be achieved by the application of electrical paddles to the chest of the patient or directly to the heart tissue, if the chest is open during surgery.

More recent improvements have lead to the development of implantable defibrillators, which monitor the heart for arrhythmias an automatically initiate defibrillation when a tachyarrhythmia occurs. Such devices often incorporate electrodes that are located on the epicardium or parietal pericardium, being connected to a defibrillation unit by means of a lead.

However, major surgery is generally necessary to implant and affix present defibrillator lead systems into their desired position. For example, a median sternotomy or lateral thoracotomy may be required. Such procedures can be very traumatic to the patient, and may have adverse side effects such as surgical complications. Because of the significant surgical risks of the present lead systems, many patients who might otherwise benefit from the use of an implantable defibrillator are excluded from using one.

The issue of fixation of leads in a desired position in the body can be important for any implantable device, but it is especially important for defibrillator leads, since to prevent a short circuit, the electrodes of the typical pair of defibrillator leads cannot be allowed to come into close proximity to each other. When implanting paddle electrodes via conventional thoracotomy or sternotomy, there is adequate access to the leads and surrounding tissues to secure the leads with suture to those tissues in order to fixate their position. However, in the case of a paddle electrode placed through a small incision using a limited surgery technique, or a deployable lead that has been placed through a small aperture, suturing by hand is not possible due to the lack of access. A deployable lead is one that can be inserted into the body in a collapsed configuration, and later be expandable to a new configuration, which has dimensions that are larger than the incision which provided entry of the lead into the body.

Another difficulty involved in fixating leads to the epicardium, when compared to fixating leads to the endocardium, relates to the lack of trabeculae for engagement with tines, and also the presence of coronary blood vessels that must be avoided if one attempts to use screw or hooks that penetrate the tissue.

By this invention, a lead is preferably attached to the pericardium, and not the epicardial surface of the heart, thus decreasing the likelihood of complications such as coronary vessel damage, myocardial laceration or excessive hemorrhage. The described tool allows the positioning of the lead to its desired location on the pericardium, the grasping of pericardial tissue, withdrawing the pericardium away from the underlying heart and then the safe delivery of a fastener, which attaches and fixates the lead to the previously grasped tissue. The fastener may be attached firmly, yet relatively atraumatically, since only fibrous tissue is grasped and penetrated. One possible fastener device is one that has no sharp edges exposed to tissue once it has been applied. The grasping jaws may be an integral component of the tool, or the tool may provide a hollow lumen for delivery of different grasping tools, which could then be used in conjunction with the fastening tool. The tool may also incorporate a small fiber optic scope for visualization of the procedure.

Thus, the invention of this application exhibits significant advantages over prior art methods for implanting defibrillation leads, particularly adjacent the heart, as shown in Chin et al. U.S. Pat. No. 4,865,037 or Person U.S. Pat. No. 3,999,555, for example. It also exhibits significant advantages over existing surgical clip appliers (Ethicon, U.S. Surgical) by allowing a fastener to be placed safely on one tissue without risk of piercing or damaging an underlying structure.

Other objects and advantages of the present invention will become apparent as the description proceeds.

DESCRIPTION OF THE INVENTION

In accordance with this invention, a method is provided for implanting a defibrillation lead at the heart, which comprises the following steps:

After introducing the lead into the thoracic cavity and performing any necessary dissection of tissue around the pericardium, the electrode portion of the lead is positioned by the tool on the pericardium in its desired location. Using one set of grasping jaws integral to the tool, a small portion of pericardial tissue is gripped, and the pericardial tissue is drawn away from the epicardial surface of the heart and toward the tool so that it lies within a second set of jaws. The outer, second set of jaws hold the fastener, which is then applied through the pericardial tissue and a portion of the lead. By drawing the pericardium away from the surface of the heart and within the outer second set of jaws, the fastener can be applied safely without risk of piercing the heart or concern about the angle between the shaft of the tool and the pericardium.

Preferably, the above-described fastener used to fixate the defibrillation patch may be of such construction that when fully closed, all sharp ends are buried in part of the fastener.

In accordance with the invention the fastener member may have one open end and another sharp, pointed end. Upon attaching, the sharp, pointed end will mate with the open end, burying the pointed end into it. Alternatively, the fastener member may have one soft, closed end and another sharp, pointed end. Upon attaching, the sharp, pointed end will poke into the soft end, burying the pointed end into it.

Fasteners of the above construction could be made of titanium, for example. The fasteners may be made to be radiopaque, so that they are visible on x-ray and fluoroscopy, for effective observation both during implantation and later follow-up. If radiopacity is desired, they could be made of tantalum, for example. Another possibility is to have an inner core of metal, for example tantalum, and an outer covering of plastic or rubber. A variation of this possibility is to have a core of metal with a partial covering of plastic or rubber, with the metal exposed on the pointed end but not on the open or soft end.

The lead may have openings through which one end of a fastener may be placed. Alternatively, the lead may have features that may be easily grasped by the fastener. As another possibility, the lead may have holes through which pericardium may be grasped by the first set of jaws. The fastener may then be applied to the pericardium itself, and would in that case be of a larger size than the hole so that it is captured and cannot slip through the hole.

The tool used in accordance with this invention for securing leads to a tissue site preferably comprises a first pair and a second pair of jaws, the first being for grasping pericardium and pulling it into the path of a fastener held in the second pair of jaws. Once the pericardial tissue is grasped by the jaws, the jaws can either be released, or the jaws with grasped tissue can be retracted into the instrument, pulling the tissue into a relationship with the fastener held on the second pair of jaws such that closing the second pair of jaws would result in applying the fastener to the pericardial tissue, thereby fixating the lead in place to the pericardium. The motion of retracting the tissue into the instrument may be followed by any one of the following: the tissue may be pushed away from the tool by the jaws, and then released; the tissue may be held in place indefinitely without further action of the fastening tool; the second pair of jaws may be closed, applying the fastener, and fixating the lead in place to the pericardium. These actions could be performed by one or more triggers built into the handle of the tool.

The tool could also incorporate a small fiber optic scope, which could be positioned a small distance behind the two sets of jaws. In this configuration, the scope would provide a view, displayed on a monitor, of the action of the tool grasping tissue and applying the fastener, to further ensure safety and effective fixation.

Another variation of the apparatus would be to eliminate the inner grasping jaws as an integral, fixed part of the tool, and instead provide a hollow lumen through which any number of small diameter endoscopic tools with different grasping tips could be passed. These different grasping instruments could then be used as the inner jaws to grasp and mobilize the tissue, and the fastener applied as described above.

The design of the tool is intended to allow its use in the body via a large incision, such as a lateral thoracotomy, or through a small aperture, such as a 10 or 12 mm trocar.

Although the tool, as described above, is used to fixate a defibrillation patch to the pericardium, it should be noted that it has much broader applications, and could be used to attach different types of clips or fasteners to any tissue in which it is preferable to first grasp and control the tissue and withdraw it away from underlying or surrounding structures before applying the fastener.

A further explanation of the invention is provided in the following description and claims, and is illustrated in the accompanying drawings.

BRIEF DESCRIPTION OF THE DRAWINGS

FIG. 1 is an enlarged view of a fastener constructed in accordance with the principles of the present invention, in its open position.

FIG. 2 is a view of the fastener of FIG. 1, with the fastener in its closed position.

FIG. 3 is an enlarged view of a fastener in accordance with another form of the invention, its open position.

FIG. 4 is a view of the fastener of FIG. 3, with the fastener in its closed position.

FIG. 5A is a top view of a fastening tool constructed in accordance with the principles of the present invention, with the grasping jaws illustrated in an extended position.

FIG. 5B is a fragmentary view of the distal end of the fastening tool of FIG. 5A, showing the jaws in their closed position.

FIG. 5C is a fragmentary view thereof, showing the jaws in another position.

FIG. 5D is a fragmentary view thereof, showing the second pair of jaws in a different position.

FIG. 5E is an elevational view of the tool of FIG. 5A.

DETAILED DESCRIPTION OF THE ILLUSTRATIVE EMBODIMENTS

Figure 6A:
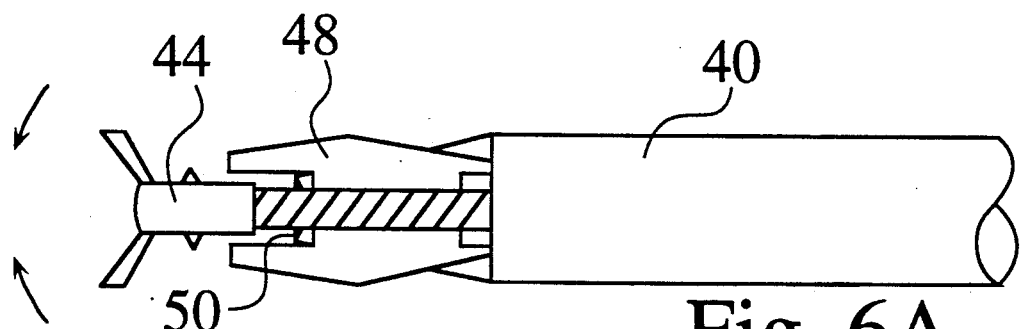
FIGS. 6A-6D are enlarged views of the inner grasping jaws and outer fastening jaws in different operations.
Figure 6B:
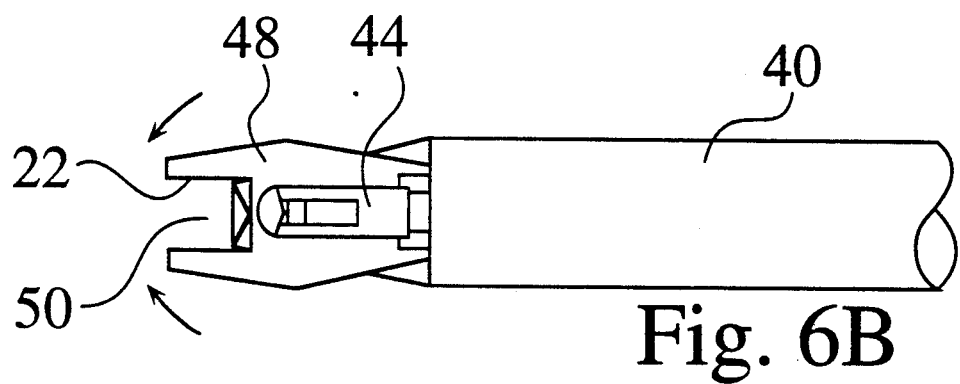

Referring to FIGS. 1-4, the fasteners 20,22 illustrated therein may have a closed shape that is substantially rectangular (FIGS. 1 and 2) or round (FIGS. 3 and 4). As illustrated, fastener 20 has one end 24 that is sharp and pointed, and its opposite end 26, which may or may not have a sharp edge, has an opening 28 for receiving sharp end 24. Thus when the fastener is closed, the sharp and pointed end 24 is enclosed by end 26. In this manner, the closed fastener does not have any exposed sharp points or edges.

The fastener 22 of FIGS. 3-4 has a sharp pointed end 30 and an opposite end 32 which is made of softer material in which the pointed end 30 can be buried.

Both types of fasteners may be made so that the jaws of the tool push the ends together. Alternatively, they could be made of a type of spring metal, in which case the jaws of the tool would apply an opening force against the fastener to hold the fastener open until it was ready to be applied. The fasteners may be made of metal that is radiopaque so that they can be viewed on x-ray or fluoroscopy and may have a partial covering of plastic or rubber, with the sharp ends uncovered.

Referring to FIGS. 5A-5E, a fastening tool 36 is shown therein, comprising a handle 38 at its proximal end, a shaft 40 extending forwardly from handle 38, a lever 42 carried by the handle 38 for actuating a first pair of jaws 44, and a trigger 46 carried by handle 38 for actuating a second pair of jaws 48. Jaws 48 and 44 may be rotated by rotating knob 49.

In FIGS. 5A and 5E, the jaws 44, 48 are shown at rest. In FIG. 5B, the grasping jaws 44 are closed in response to moving lever 42 to its first active position B. FIG. 5C shows grasping jaws 44 retracted towards the tool and outer jaws 48 in response to moving lever 42 to its second active position C. Lever 42 can remain locked indefinitely in either of its active positions B, C using an internal ratchet, or be released back to position A. FIG. 5D shows the fastener action of the outer jaws in response to the squeezing of trigger 46.

Figure 6C:
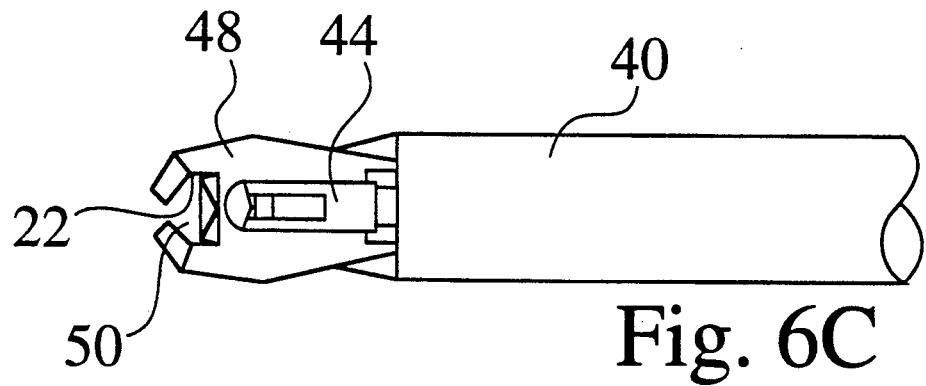
Figure 6D:
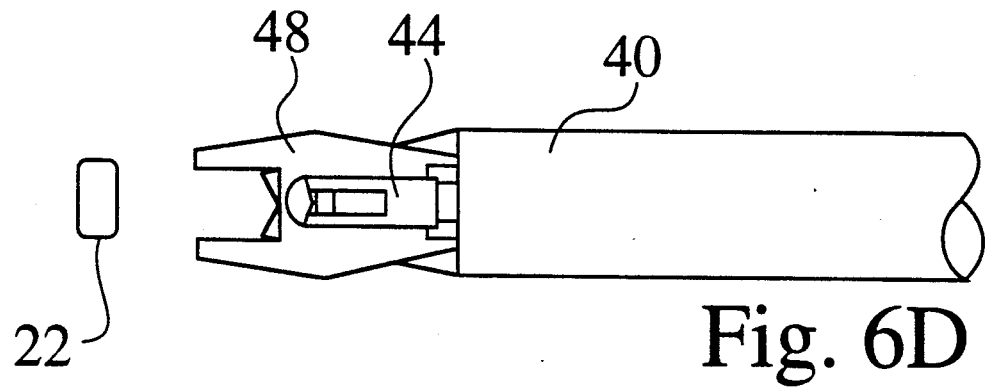

More detailed illustrations of the jaws and fastener actions are found in FIGS. 6A-6D. Referring to these figures, FIG. 6A shows the grasping jaws 44 in their extended position. From this position, the jaws 44 can grab the pericardium, close and then be retracted to pull the pericardium back so that it lays within the opening 50 of the outer jaws 48. Outer jaws 48 carry a fastener member 22 and once the pericardium is pulled into opening 50, outer jaws 48 squeeze the fastener 22 (FIG. 6C) to close the fastener 22 as required (FIG. 6C). Once the fastener 22 is closed, as illustrated in FIG. 6D the outer jaws 48 are opened to release the fastener 22 from the tool.

Figure 7:
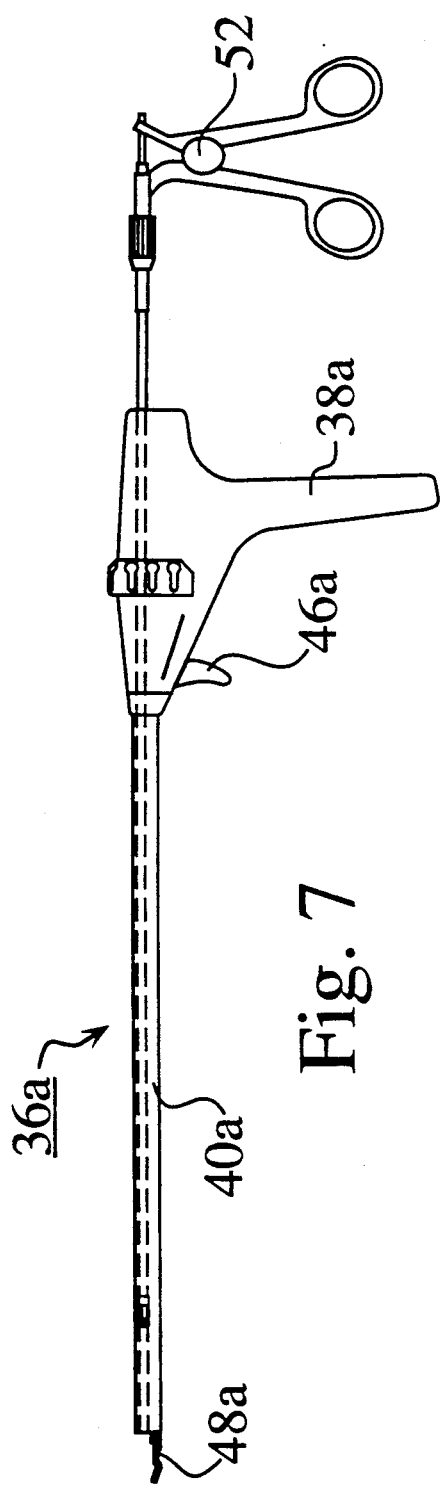
FIG. 7 is an elevational view of a fastening tool constructed in accordance with another form of the present invention, utilizing a hollow lumen through which a small diameter endoscopic tool can be passed.
Figure 8:
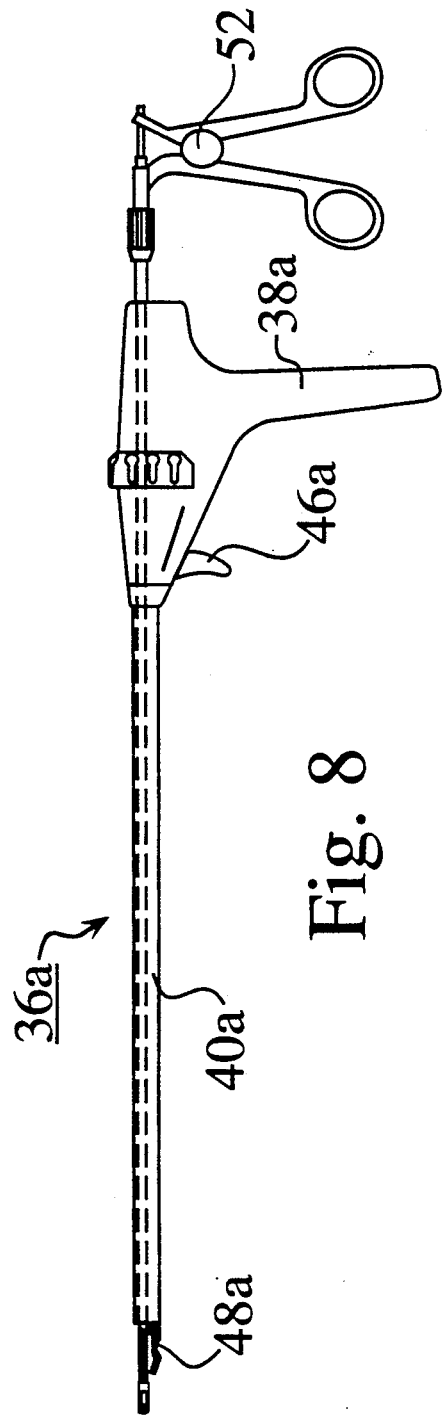
FIG. 8 is similar to FIG. 7, but shows the endoscopic tool in another position.

In FIGS. 7 and 8 a modified form of fastening tool 36a is shown. In this modified form, handle 38a and shaft 40a have a hollow lumen through which any number of small diameter endoscopic tools with different grasping tips could be passed. Thus instead of utilizing grasping jaws 44 as with the tool of FIGS. 5A-5E, the FIGS. 7-8 tool uses an endoscopic tool 52 which is inserted through the lumen and carries its own grasping tips. Trigger 46a operates grasping jaws 48a in the same manner that trigger 46 of the FIGS. 5A-5E embodiment operates grasping jaws 48, to apply the fastener 22.

Figure 9:
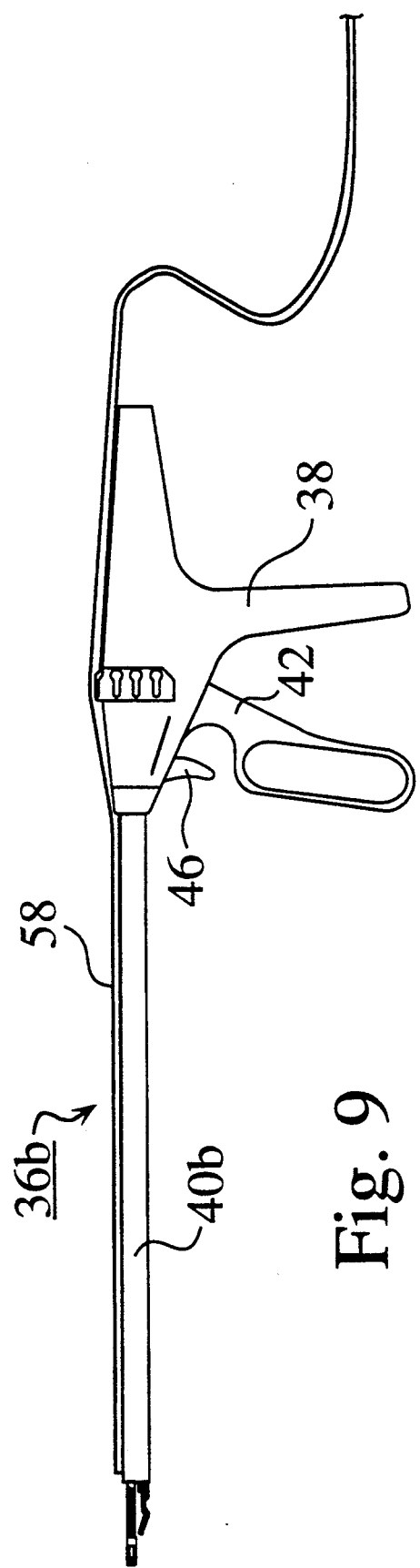
FIG. 9 is an elevational view of a tool constructed in accordance with a further form of the invention, with the addition of a fiber optic scope positioned adjacent the grasping and fastening jaws of the tool.

FIG. 9 illustrates a fastening tool 36b that is similar to fastening tool 36 of FIGS. 5A-5E, with the addition of a fiber optic scope 58 positioned a small distance behind the grasping and fastening jaws. Fiber optic scope 58 provides a view of the action of the tool on a display monitor.

FIGS. 10 through 15 are schematic views of sequential steps in the method of implanting and fixating a defibrillation electrode 60 to the pericardium 62. Defibrillation electrode 60 has a central electrode portion 64 and a surrounding rim 66 which defines a number of equally spaced openings 68.

Figure 10:
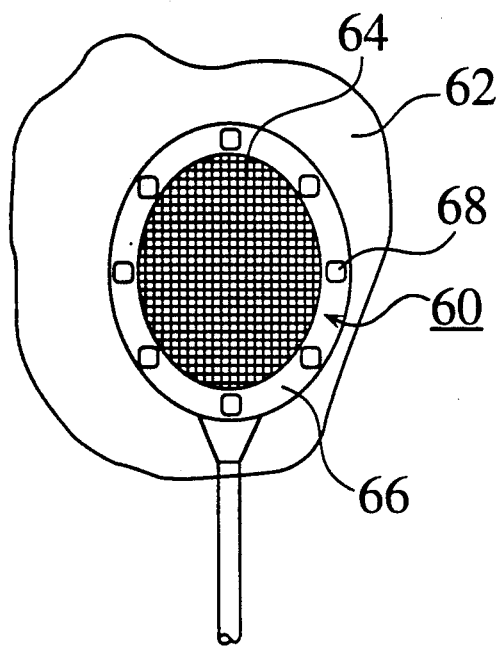
FIGS. 10-15 are schematic views of steps in the method of implanting an electrode in accordance with the principles of the present invention.
Figure 11:
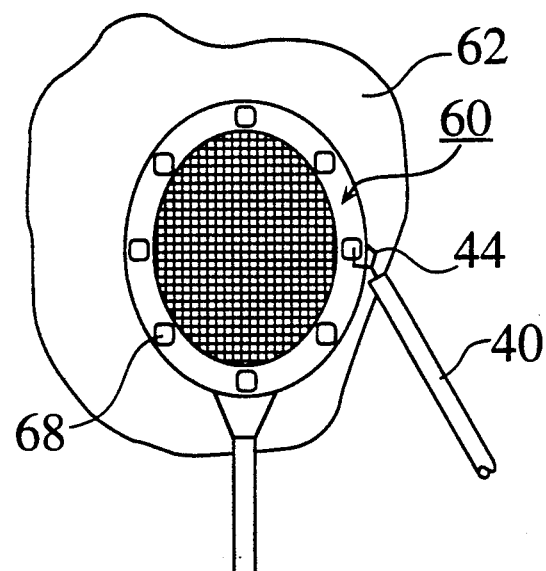
Figure 12:
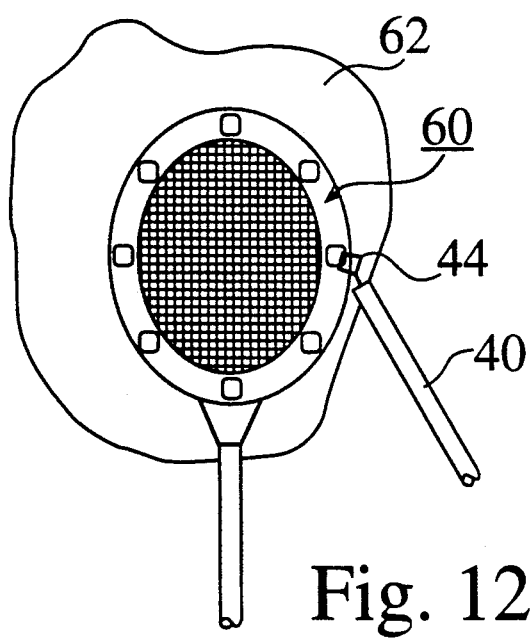
Figure 13:
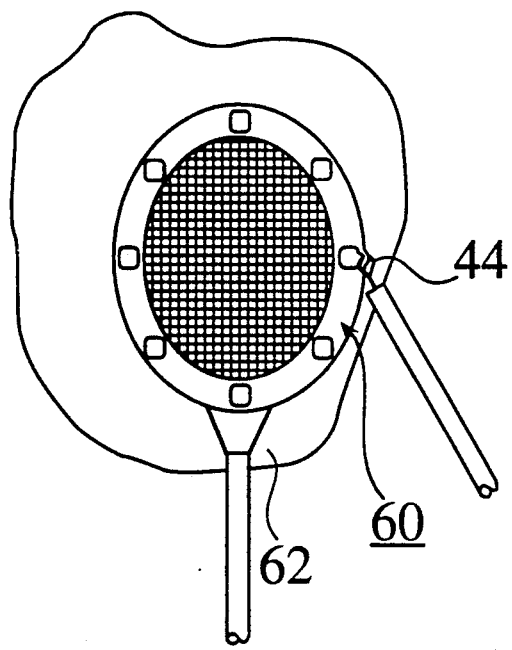
Figure 14:
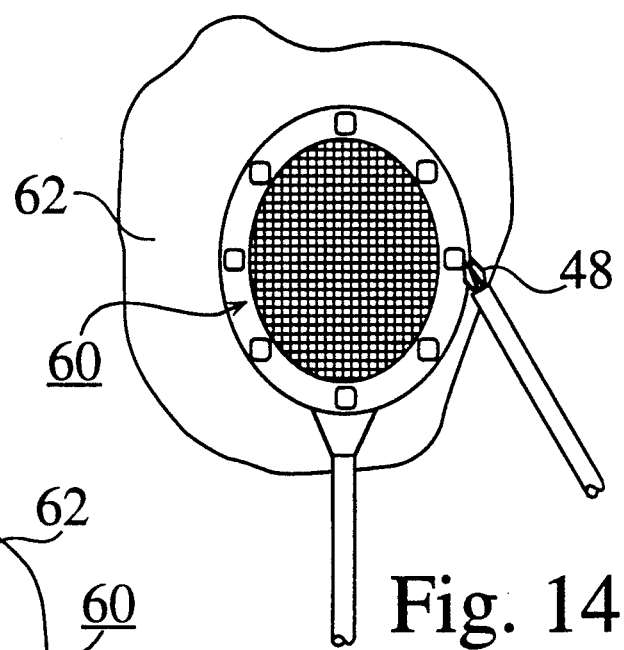
Figure 15:
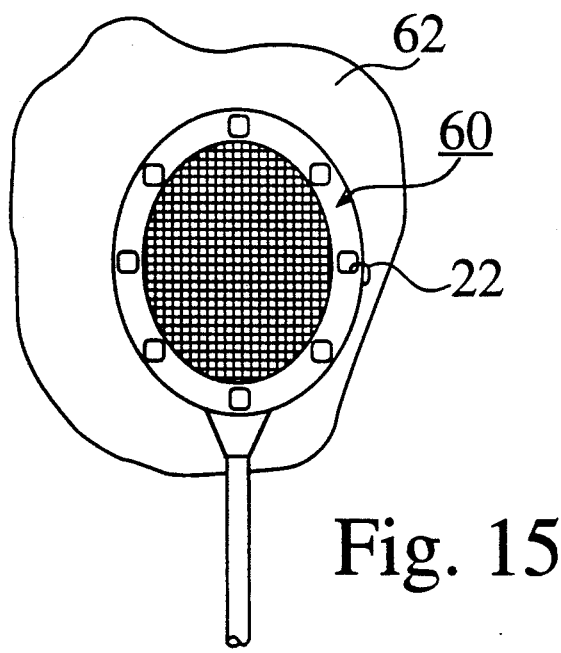

FIG. 10 shows the lead in proximity to the pericardium after being introduced into the thoracic cavity. FIG. 11 shows the lead being positioned in its desired location on the pericardium 62 using the fastening tool. The lead may be positioned by grasping a portion of the lead with the inner grasping jaws 44, or by hooking an apparatus or hole 68 in the lead with one of the outer fastening jaws. FIG. 12 shows, after the lead has been properly positioned, the pericardium 62 being grasped by the inner grasping jaws 44. The portion of the lead to be fastened to the pericardium may also be held by the grasping jaws or may be hooked by one of the fastening jaws. FIG. 13 show the grasping jaws 44 being withdrawn, pulling the pericardium 62 away from the surface of the heart. FIG. 14 shows the fastener being applied to the withdrawn pericardium and lead, thereby fixating the lead to the pericardium. FIG. 15 show the tool removed and the fastener 22 attached to the pericardium 62 and lead 60. The above described steps may be repeated in order to place several fasteners to the lead.

Figure 16:
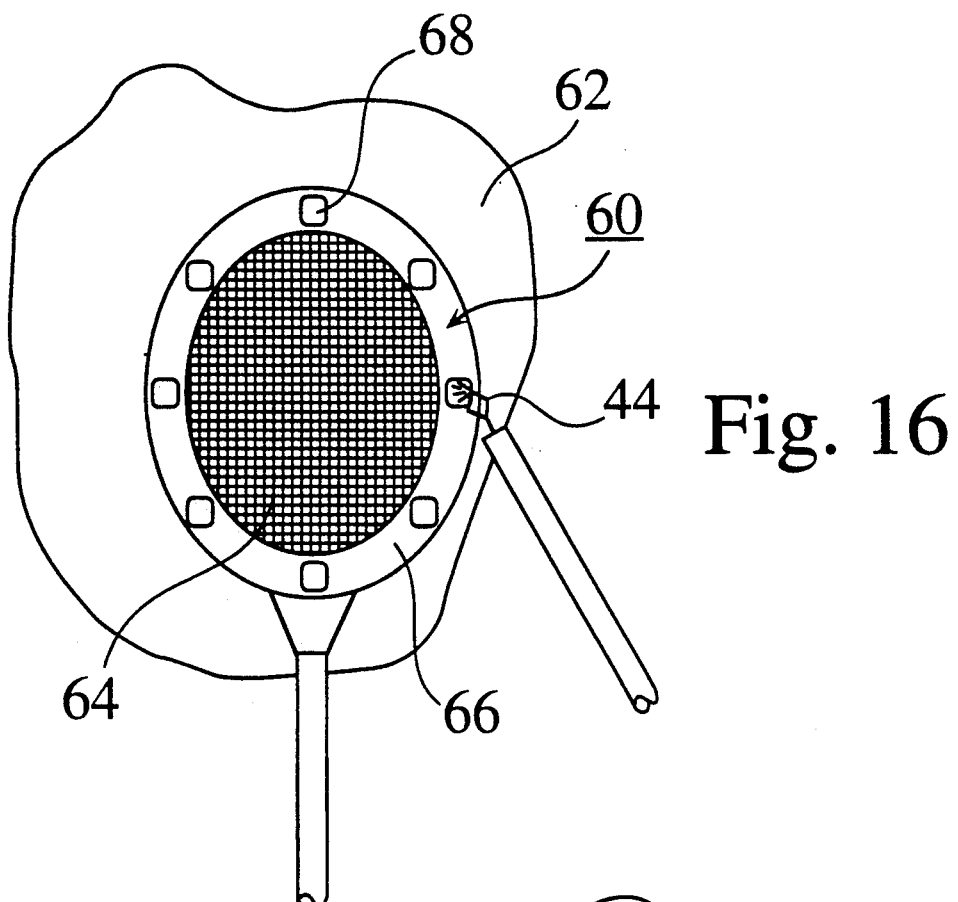
FIGS. 16-17 are schematic views of another method thereof.
Figure 17:
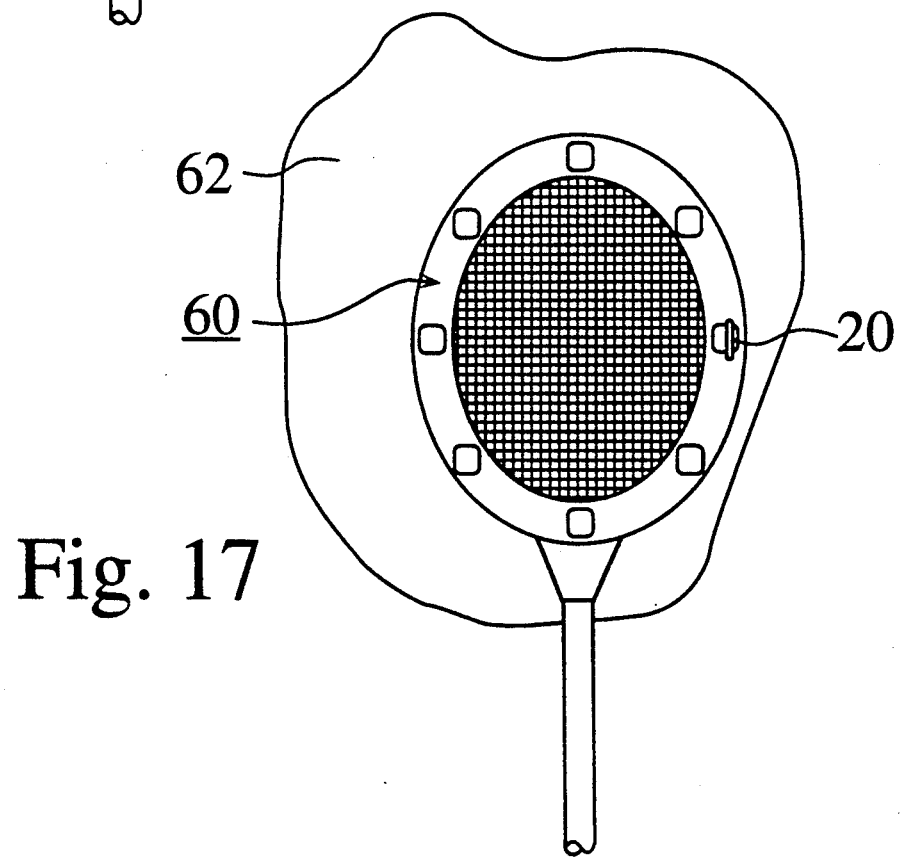

FIGS. 16-17 illustrate another method of fixating a lead 60 to the pericardium in accordance with this invention, in which both grasping jaws are positioned through a hole 68 in the lead, the pericardium 60 is grasped and withdrawn back through the hole 68 and the fastener is attached only to the pericardium and not the lead. In this case, the fastener would necessarily be large enough so that it would not fit back through the hole 68 in the lead.

Although illustrative embodiments of the invention have been shown and described, it is to be understood that various modifications and substitutions may be made by those skilled in the art without departing from the novel spirit and scope of the present invention.

What is claimed is:

1. A tool which comprises:
   a first pair of jaws for grasping membranous tissue and drawing said tissue away from other tissue and towards said tool; and
   a second pair of jaws arranged in longitudinal sliding relation with said first pair of jaws and releasably carrying a fastener member for delivering and emplacing said fastener member to and in said membranous tissue, said fastener member having an open position and a closed position, in which said fastener member has in its open position a sharp end and an opposite end that is open to receive said sharp end, said sharp end being buried within said opposite end in its closed position, said fastener member being moved from said open position to the closed position by bending caused by said second pair of jaws.

2. A tool which comprises:
   a first pair of jaws for grasping membranous tissue and drawing said tissue away from other tissue and towards said tool; and
   a second pair of jaws arranged in longitudinal sliding relation with said first pair of jaws and releasably carrying a fastener member for delivering and emplacing said fastener member to and in said membranous tissue, said fastener member having an open position and a closed position, in which said fastener member has in its open position a sharp end and an opposite end that is open to receive said sharp end, said sharp end being buried within said opposite end in its closed position, said fastener member being moved from said open position to the closed position by bending caused by said second pair of jaws.

* * * * *